United States Patent [19]
de Haan et al.

[11] Patent Number: 5,756,104
[45] Date of Patent: May 26, 1998

[54] LIPOSOME-CONTAINING INTRANASAL VACCINE FORMULATION

[75] Inventors: Aalzen de Haan; Harmen J. Geerligs; Jan C. Wilschut, all of Weesp, Netherlands

[73] Assignee: Duphar International Research B.V., Weesp, Netherlands

[21] Appl. No.: 461,768

[22] Filed: Jun. 5, 1995

Related U.S. Application Data

[63] Continuation of Ser. No. 137,218, Oct. 18, 1993, abandoned, which is a continuation of Ser. No. 982,423, Nov. 27, 1992, abandoned, which is a continuation of Ser. No. 645,456, Jan. 24, 1991, abandoned.

[30] Foreign Application Priority Data

Jan. 29, 1990 [NL] Netherlands ............................ 9000207

[51] Int. Cl.$^6$ ...................... A61K 39/145; A61K 39/165; A61K 39/295; A61K 9/127
[52] U.S. Cl. ........................... 424/206.1; 424/193.1; 424/196.11; 424/202.1; 424/212.1; 424/450; 424/283.1
[58] Field of Search .................... 424/206.1, 193.1, 424/450, 283.1, 196.11, 197.11, 201.1, 202.1, 203.1, 212.1

[56] References Cited

U.S. PATENT DOCUMENTS

| | | | |
|---|---|---|---|
| 4,053,585 | 10/1977 | Allison et al. | 424/239.1 |
| 4,148,876 | 4/1979 | Almeida et al. | 424/89 |
| 4,196,191 | 4/1980 | Almeida et al. | 424/89 |
| 4,261,975 | 4/1981 | Wardle et al. | 424/89 |
| 4,310,550 | 1/1982 | Wolff, III et al. | 424/365 |
| 4,323,561 | 4/1982 | Nowotny | 424/92 |
| 4,395,394 | 7/1983 | Wolff, III et al. | 424/88 |
| 4,522,811 | 6/1985 | Eppstein et al. | 514/2 |
| 4,565,696 | 1/1986 | Heath et al. | 514/2 |
| 4,684,625 | 8/1987 | Eppstein et al. | 514/19 |
| 5,026,557 | 6/1991 | Estis et al. | 424/450 |
| 5,100,662 | 3/1992 | Bolcsak et al. | 424/283.1 |

FOREIGN PATENT DOCUMENTS

| | | | |
|---|---|---|---|
| 0158880 | 10/1985 | European Pat. Off. | A61K 9/50 |
| 0324455 | 7/1989 | European Pat. Off. | A61K 47/00 |
| 0356340 | 2/1990 | European Pat. Off. | |
| 0155625 | 9/1995 | European Pat. Off. | |
| 2066203 | 7/1981 | United Kingdom | G01N 33/50 |
| 8905631 | 6/1989 | WIPO | A61K 9/127 |

OTHER PUBLICATIONS

European Search Report for NL9000207.
Shek et al (1981) Immunology 45:349–356.
Lowell et al. (1988) J. Expt. Medicine 167:658–663.
Chemical Abstracts, vol. 96, No. 23, 7 Jun. 1982, p. 499, Abstract No. 197652a, Shek et al "Immune Reponse Mediated . . . ".
Fraser Smith et al. (1983) Infect. Immunity39(1):172–178.
Gregoriadis et al. (1987) Vaccine 5:145–151.
Therien et al. (1989) Immunol. Lett. 22:253–258.
Gregoriadis (1990) Immunology Today 11(3):89–97.
Shek (1984) in Mullen ed *Immunotoxicology* pp. 103–125, Springer–Verlap.
Van Rooijen et al. (1977) Immunol. Commun. 6(5):489–498.
Allison et al. (1976) Nature 252:252.
Pierce et al. (1984) Rev. Infect. Dis. 6(4):563–566.

*Primary Examiner*—Kay K.A. Kim
*Attorney, Agent, or Firm*—Watson Cole Stevens Davis, P.L.L.C.

[57] ABSTRACT

The present invention relates to a vaccine formulation for intranasal or inhalation administration, and to the preparation thereof, which formulation contains antigenic material freely mixed with empty liposomes.

11 Claims, 3 Drawing Sheets

LIPOSOME-CONTAINING INTRANASAL VACCINE FORMULATION

This application is a continuation of application Ser. No. 08/137,218, filed Oct. 18, 1993 now abandoned; which in turn is a continuation of application Ser. No. 07/982,423, filed Nov. 27, 1992, now abandoned; which in turn is a continuation of application Ser. No. 07/645,456, filed Jan. 24, 1991, now abandoned.

This invention relates to liposome-containing vaccine formulations for intranasal or inhalation administration and to the prepration of such formulations. The invention relates in particular to a vaccine of this type to prevent influenza infections in humans. However, the invention is not restricted to application in influenza vaccines.

It is the object of vaccination against infectious diseases to prevent or at least restrain infection of the vaccinated subject by stimulating an immune response against the infectious agent through introduction of an antigen formulation derived from the particular pathogen. Ideally, the induced immune response should consist of two components, a humoral response (the production of antigen-specific antibodies) and a cellular response (the generation of specific cytotoxic T lymphocytes, capable of eliminating cells infected by the pathogen).

Many vaccination procedures involve the administration of a formulation containing inactivated or attenuated whole pathogen. However, there is a considerable disadvantage to vaccination with whole pathogen, since such preparations, even though they are usually highly immunogenic, may have undesirable side effects. This explains the current trend towards the use of well-defined subunit or synthetic vaccines, substantially lacking the adverse side effects of the whole infectious agent. However, compared to whole pathogen, subunit or synthetic vaccines are often not very immunogenic, at least in the absence of an added adjuvant. Adjuvants are substances or materials administered in conjunction with the antigen so as to stimulate the immune response against that antigen. There is a need for appropriate adjuvants which would boost the immune response against subunit or synthetic antigens without causing undesirable side effects.

Influenza vaccine formulations have contained for a long time, and in some cases still contain, inactivated or attenuated whole virus. Such formulation may have considerable side effects, most notably fever and reactions at the site of injection. Nowadays, vaccination is usually done with a subunit formulation. This subunit vaccine, which causes less side reactions, only contains the two major surface antigens of the virus, the hemagglutinin (HA) and the neuraminidase (NA), in a more or less purified form. In most current vaccine formulations there is no added adjuvant present.

The inactivated or attenuated whole influenza virus vaccine as well as the subunit vaccine are usually administered via a single intramuscular (i.m.) injection. The protection against influenza infection, achieved by either vaccination procedure, is comparatively low, particularly in elderly people. The relatively low efficacy of vaccination against influenza is due in part to the high antigenic variability of the virus. However, there is reason to believe that the protection against influenza infection by vaccination can be improved by stimulation and/or modification of the immune response against the vaccine.

In the case of influenza, or in general in cases in which the infection is contracted via the respiratory tract, strategies for improved vaccination efficacy should aim at the generation of not only an adequate T-cell-dependent IgG response in the circulation, but also at a local immune response (secretory IgA) in the lungs and nasal cavity as a first line of defense against invading infectious virus. Furthermore, a cellular immune response (cytotoxic T-cells) might also be important, particularly in restricting the infection. It has been demonstrated that administration of influenza vaccine via i.m. injection (the current route of administration) does not result in a local IgA response in the respiratory tract.

The present invention discloses that the presence of liposomes in an intranasal or inhalation influenza subunit vaccine formulation not only stimulates the IgG response in the circulation, relative to i.m. immunization with the free subunit vaccine, but also generates a local IgA response in the respiratory tract.

Liposomes are artificial lipid vesicles which have been studied extensively as a model for biological membranes and as a potential carrier system for drugs and other biologically active substances. Liposomes can be prepared in various manners starting from a single phospholipid or mixtures of various phospholipids, whether or not in combination with a sterol, for example, cholesterol. By a suitable choice of methodologies, comparatively homogeneous compositions of unilamellar, oligolamellar or multilamellar vesicles can be prepared, the diameter of which can be varied within certain limits. Each type of liposome has one or more aqueous compartments separated from the external medium by one or more concentric membranes, each of which comprising a lipid double layer. Water-soluble substances can be encapsulated within these internal compartments.

The basis for the adjuvant action of liposomes is not known. However, it is widely believed that liposomes in vaccine formulations serve the function of an antigen carrier. Thus, the adjuvant action of liposomes may be due to the natural targetting of liposomes in the body to cells belonging to the reticulo-endothelial system (RES), in particular to macrophages in the liver, spleen, bone marrow and lungs. Macrophages are known to play a central role in the immune response as antigen-presenting cells (APC's). Optimal antigen presentation is of fundamental importance for generation of an effective T-cell-dependent humoral immune response, since the helper T-cells, which are critically involved in this type of immune response, are not activated by direct interaction with the antigen, but only by antigen expressed at the surface of APC's.

The adjuvant activity of liposomes has initiated many attempts to improve vaccine formulations, among which influenza vaccine formulations, by inclusion of liposomes. However, without exception, in these formulations the antigen is physically associated with the liposome, either by encapsulation within the aqueous interior of the liposomes or by coupling to the external surface of the liposomes. For example, European patent application No. 89402344.9 (publication No. 0356340) discloses a vaccine formulation in which the antigen is present in affinity association with the surface of liposomes. It is not surprising that these previous liposomal vaccine formulations have been based on the generation of an antigen-liposome complex, since an antigen-carrier function of the liposome obviously calls for some kind of association of the antigen with the carrier. The vaccine formulation disclosed in the present invention does not involve association of the antigen with the liposome. By contrast, the formulation comprises liposomes and non-enclosed antigenic material. It is very surprising that with such a vaccine a considerably higher immune response is obtained than with antigen in the absence of liposomes (Examples 1 and 2). It is even more surprising that the stimulation of the immune response by the liposomes is observed when the liposomes and the antigen are administered separately in time (Example 3). This observation suggests that the stimulatory effect of the liposomes in this case may not be due to the presumed function of liposomes as an antigen carrier. It is a great advantage of the formulation according to the invention that it is not necessary to take care that the liposomes and the antigens are associated with each other.

The efficacy of the known liposomal vaccine formulations, mentioned hereinbefore, has been tested usually after intramuscular, subcutaneous or intraperitoneal administration to animals, usually mice. By contrast, the vaccine formulation disclosed in the present invention is administered intranasally or by inhalation, and it elicits a significant local IgA response in the respiratory tract. Only in one instance a liposomal influenza vaccine formulation has been administered intranasally (Torchilin et al. in G. Gregoriadis (editor), "Liposomes as Drug Carriers" (1988), pp. 229–230, John Wiley & Sons, Ltd). However, in this particular formulation the antigen was encapsulated within the aqueous compartment of liposomes, whereas in the vaccine formulation according to the present invention antigen and liposomes are mixed freely. The vaccine formulation described by Torchilin et al. has not been tested for IgA production in the respiratory tract.

The route of administration of the vaccine according to the invention is of particular advantage in vaccination against those diseases that are not normally life-threatening, such as influenza. In these cases, where vaccination is often considered a matter of "convenience", the inconvenience of an intramuscular injection may constitute an important barrier for an effective implementation of vaccination programmes.

The invention will be illustrated mainly with influenza virus subunit antigen as an example. However, Examples 5 and 6 show that the invention is not restricted to influenza vaccine formulations. The liposomes may also be mixed with other antigens or with a mixture of different antigens.

It has been found that the stimulatory effect of liposomes is significant when the mass ratio of liposomal material to antigenic material is at least 5; optimal ratio's are higher, in the order of 100–1000.

The liposomes to be used according to the invention are built up preferably from one or more phospholipids, for example phosphatidylcholine (PC), and optionally a sterol, such as cholesterol.

It has further been found to be of critical importance that the liposomes contain a component which gives the liposomes a net negative surface charge. Examples of components suitable for this purpose include dicetylphosphate (DCP), phosphatidic acid (PA) or phosphatidylglycerol (PG).

The liposomes in the vaccine according to the invention are preferably of the multilamellar type. They can be prepared in a simple manner by dispersing a dried lipid mixture in a buffered salt solution, such as phosphate-buffered saline (PBS). Optionally, the formed liposomes may be extruded, for example through a polycarbonate Unipore filter, to produce a more homogeneous distribution in the size of the liposomes.

The preparation and use of the vaccine according to the invention will now be described in greater detail with reference to the following examples.

EXAMPLE 1

Groups of 5 mice (Balb/C) were immunised intranasally (a total volume of 50 ul was administered under slight ether anesthesia) with free antigen (group A) or free antigen mixed with empty liposomes (groups B.1 and B.2). The antigen used was an influenza virus subunit vaccine, prepared, according to methods known in the art, from influenza virus strain X-97 (a recombinant influenza strain of the $H_3N_2$ type). The liposomes comprised cholesterol (Chol), egg-yolk phosphatidylcholine (PC), and a negatively charged lipid. Two different negatively charged lipids were compared in this experiment, namely dicetylphosphate (DCP) and phosphatidylglycerol (PG). The dosage of the immunization was 1 ug of antigen (based on the hemagglutinin (HA) content of the subunit preparation determined by single-radial diffusion analysis) and 1.6 umol of liposomal phospholipid per mouse, and two immunisations were carried out, on day 0 and on day 4.

In groups B, liposomes of two different compositions were used:

(B.1): Chol/PC/DCP=5/4/1 (molar ratio)

(B.2): Chol/PC/PG=5/4/1 (molar ratio)

Serum samples were taken at the times indicated in FIG. 1 and the titres of antigen-specific IgG were determined by enzyme-linked immunosorbent assay (ELISA), known in the art.

Figure 1A:
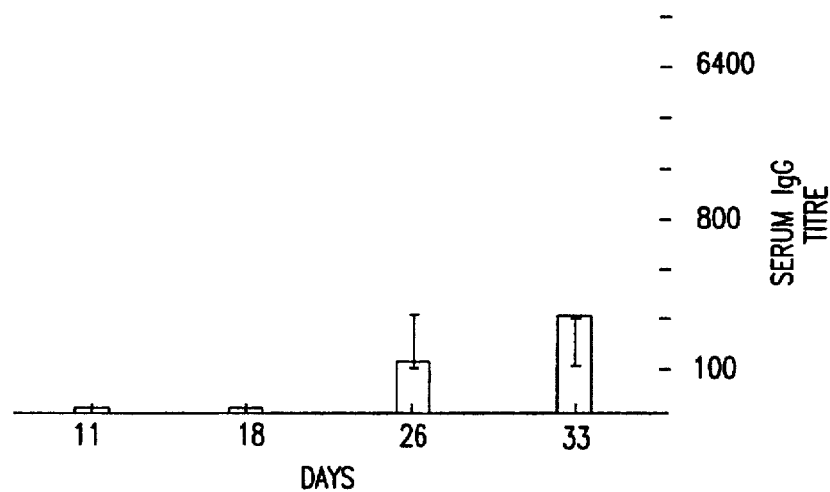
FIG. 1A shows the antigen-specific serum IgG titres in mice after i.n. immunization with free influenza subunit antigen.
Figure 1B:
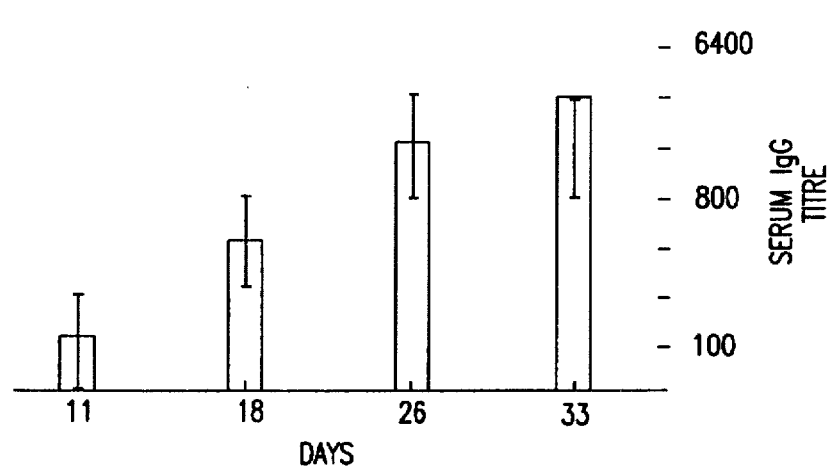
FIG. 1B shows the antigen-specific serum IgG titres in mice after i.n. immunization with antigen mixed with liposomes comprising Chol./PC/DCP in a 5/4/1 molar ratio.
Figure 1C:
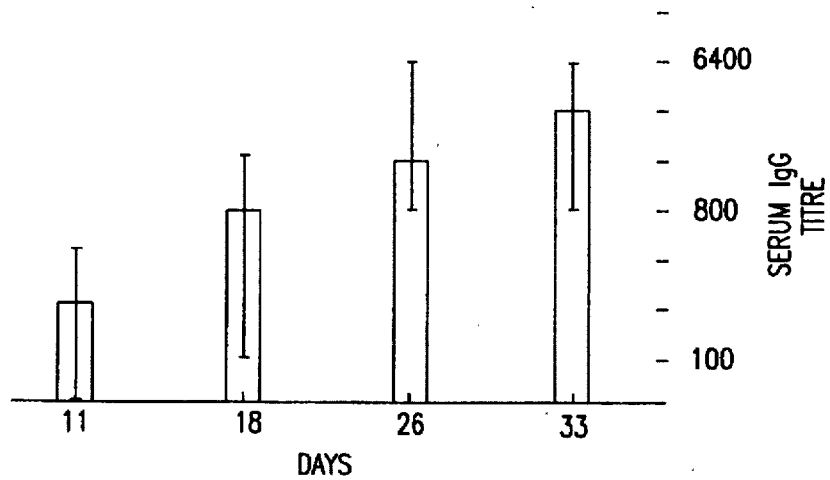
FIG. 1C shows the antigen-specific serum IgG titres in mice after i.n. immunization with antigen mixed with liposomes comprising Chol./PC/PG in a 5/4/1 molar ratio.

Immunisation with free antigen resulted in a comparatively low antigen-specific serum IgG titre (FIG. 1A). Mixing of viral antigen with empty liposomes of either type had a strongly stimulating effect on the IgG-response (FIGS. 1B and 1C).

EXAMPLE 2

Groups of 5 mice (Balb/C) were immunised intranasally, as described in Example 1. Lung washings were taken (washings, in PBS, from 5 mice, were pooled and concentrated to a final volume of 1.0 ml) 33 days after the first immunisation, and assayed for antigen-specific IgA by ELISA.

Figure 2:
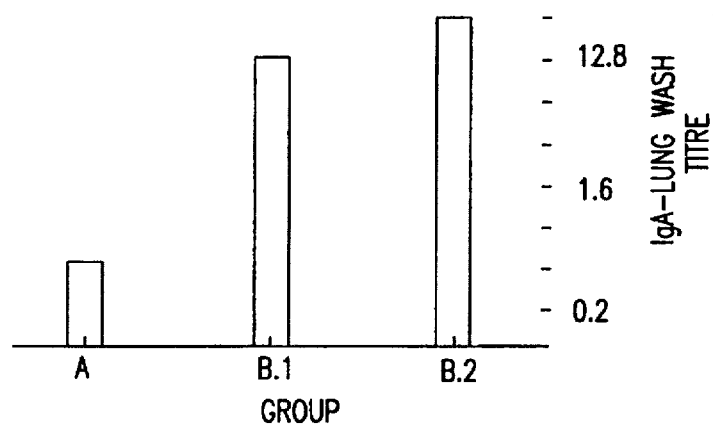
FIG. 2 shows the antigen-specific local IgA titres in lung washings from mice on day 33 after i.n. immunization free influenza subunit antigen (group A) or antigen mixed with liposomes (group B).

Significant IgA titres were measured only in the washings derived from the mice immunised with antigen mixed with empty liposomes, of either composition (FIG. 2). A very low titre was measured in the washings derived from the mice immunised with the free antigen.

EXAMPLE 3

Groups of 5 mice (Balb/C) were immunised intranasally, as described in Example 1, with the restriction that only DCP-comprising liposomes were used and that a single immunization was given. In addition to immunization of groups of mice with free antigen alone (group A) or with antigen mixed with liposomes (group B), a group of mice (C) was given liposomes and antigen separated in time, the liposomes first and the antigen 24 h after the administration of the liposomes. Serum IgG and IgA in lung washings was assayed at day 33, as described in Examples 1 and 2, respectively.

Figure 3A:
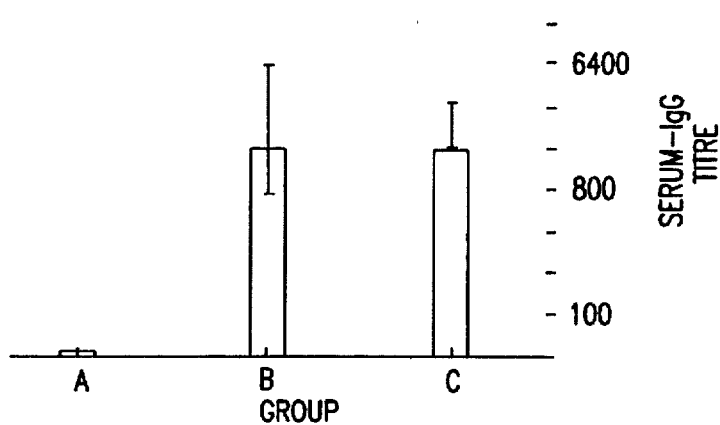
FIG. 3A shows antigen-specific serum IgG titres in mice on day 33 after a single i.n. immunization (5 μg HA) with free influenza subunit (group A), or antigen mixed with liposomes comprising Chol/PC/DCP in a 5/4/1 molar ratio liposomes (group B). Group C received liposomes first and antigen 24 hours after the liposomes.
Figure 3B:
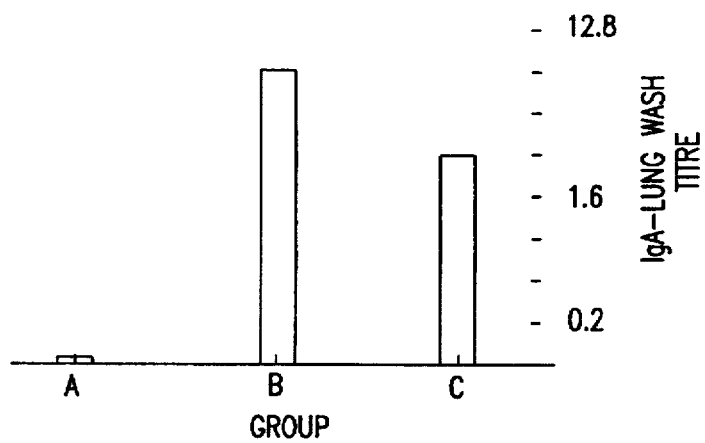
FIG. 3B shows antigen-specific lung IgA titres in mice on day 33 after a single i.n. immunization (5 μg HA) with free influenza subunit (group A), or antigen mixed with liposomes comprising Chol/PC/DCP in a 5/4/1 molar ratio (group B). Group C received liposomes first and antigen 24 hours after the liposomes.

Free antigen alone did not induce a detectable serum IgG (FIG. 3A) or local IgA response (FIG. 3B). Antigen mixed with liposomes did evoke high titres of antigen-specific serum IgG (FIGS. 3B, group B) and local IgA (FIG. 3B, group C) in the lungs. Significantly, similar results were obtained when the liposomes and the antigen were administered separately.

EXAMPLE 4

Groups of 16 mice (Balb/C) were immunized either intra-muscularly with a single dose of free antigen (group A) or intranasally with either 1 (group B) or 2 (group C) doses (on day 0 and day 4) of antigen mixed with liposomes (Chol/PC/DCP=5/4/1). A control group (D) did not receive antigen at all. The antigen used was a subunit vaccine prepared from influenza virus strain X-83 (a recombinant carrying the HA of strain A/Chile, H1N1) at 5 ug HA per dosage. Liposomes were administered at 1.0 umol of phospholipid per dosage. At day 35 after immunization the mice were challenged intranasally with infectious influenza A/Christ/157/$M_{30}M_1E_4$. Survival 7 days after the challenge was recorded.

The results (Table I) indicate that the liposomal intranasal vaccine formulation is at least as effective in protection against infection as the free subunit vaccine administered intramuscularly (the conventional vaccination protocol). A single immunization with either of the two formulations gave slightly better survival for the liposomal i.n. vaccine; a double immunization with the i.n. formulation on day 0 and 4 gave 100% survival.

TABLE I

| Group | Survival (%) |
|---|---|
| A | 81.3 (13/16) |
| B | 93.8 (15/16) |
| C | 100.0 (16/16) |

TABLE I-continued

| Group | Survival (%) |
|---|---|
| D | 50.0 (8/16)* |

*Surviving mice were very sick after 7 days, and unlikely to recover.

EXAMPLE 5

Groups of 5 mice (Balb/C) were immunised with measles antigen intranasally, as described in Example 1, with the restriction that only DCP-comprising liposomes were used. The antigen was a preparation comprising inactivated measles virus. The mice were immunized either with free antigen alone (group A) or with antigen mixed with liposomes (group B). Serum IgG and IgA in lung washings was assayed at day 33 by ELISA.

Figure 4A:
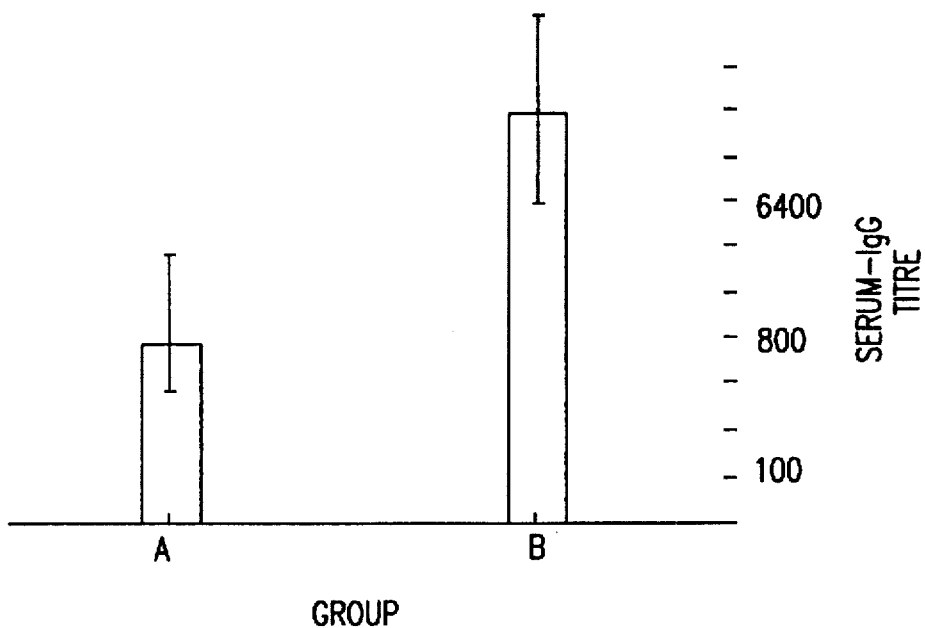
FIG. 4A shows antigen-specific serum IgG titres in mice after i.n. immunization with free measles antigen (group A), or antigen mixed with Chol/PC/DCP=5/4/1 (molar ratio) liposomes (group B). Antigen was administered twice on day 0 and day 4.
Figure 4B:
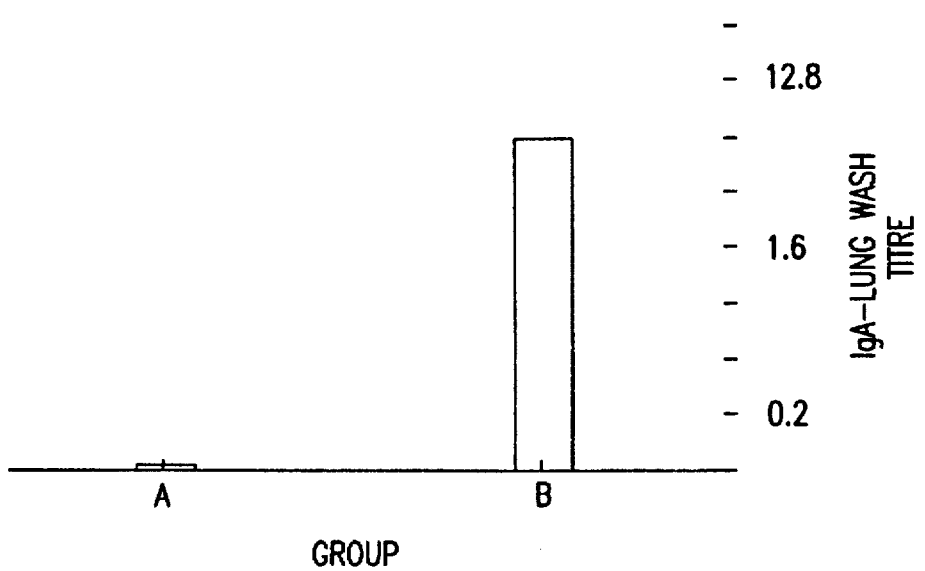
FIG. 4B shows antigen-specific lung IgA titres in mice after i.n. immunization with free measles antigen (group A), or antigen mixed with Chol/PC/DCP=5/4/1 (molar ratio) liposomes (group B). Antigen was administerd twice on day 0 and day 4.

Free antigen alone did induce a significant serum IgG response; however, the response was substantially enhanced by the presence of liposomes in the vaccine (FIG. 4A). There was no detectable local IgA response in the lungs after immunization with free antigen alone (FIG. 4B, group A). Antigen mixed with liposomes did evoke high titres of antigen-specific IgA (FIG. 4B, group B).

We claim:

1. A vaccine formulation for intranasal or inhalation administration, characterized in that the vaccine formulation comprises antigenic material and empty liposomes having a net negative surface charge, in which the antigenic material and the liposomes are substantially unassociated, and wherein the antigenic material is derived from at least one organism which is capable of infecting the respiratory tract.

2. The vaccine as claimed in claim 1, characterized in that the antigenic material consists of a combination of different antigens.

3. The vaccine as claimed in claim 1, characterized in that the mass ratio of liposomal material to antigenic material is at least 5:1.

4. The vaccine as claimed in claim 1, characterized in that the liposomes comprise at least one phospholipid.

5. The vaccine as claimed in claim 4, characterized in that the phospholipid is phosphatidylcholine.

6. The vaccine as claimed in claim 4, wherein the vaccine additionally comprises a sterol.

7. The vaccine as claimed in claim 6, characterized in that the sterol is cholesterol.

8. The vaccine as claimed in claim 1, characterized in that at least one member selected from the group consisting of dicetylphosphate, phosphatidic acid and phosphatidylglycerol is present as the charge-determining component.

9. The vaccine formulation of claim 1, wherein the antigenic material comprises the surface antigens of influenza virus.

10. The vaccine formulation of claim 1, wherein the antigenic material is derived from measles virus.

11. The method of preparing a vaccine formulation as claimed in claim 1, characterized in that dried lipid is dispersed in an aqueous medium and the resulting mixture containing liposomes is mixed with an antigen-containing solution.

* * * * *